(12) United States Patent
Newman

(10) Patent No.: US 9,370,593 B2
(45) Date of Patent: Jun. 21, 2016

(54) MODULAR MULTIFUNCTION FRAGRANCE EMITTER

(71) Applicant: Home & Garden Party, Ltd., Marshall, TX (US)

(72) Inventor: Lowell W. Newman, Hallsville, TX (US)

( * ) Notice: Subject to any disclaimer, the term of this patent is extended or adjusted under 35 U.S.C. 154(b) by 430 days.

(21) Appl. No.: 13/934,202

(22) Filed: Jul. 2, 2013

(65) Prior Publication Data

US 2015/0010293 A1   Jan. 8, 2015

(51) Int. Cl.
| | |
|---|---|
| A61M 16/00 | (2006.01) |
| F24F 3/14 | (2006.01) |
| F24F 6/00 | (2006.01) |
| A61H 33/12 | (2006.01) |
| A61L 9/03 | (2006.01) |

(52) U.S. Cl.
CPC ............. *A61L 9/032* (2013.01); *A61L 2209/12* (2013.01); *A61L 2209/134* (2013.01)

(58) Field of Classification Search
None
See application file for complete search history.

(56) References Cited

U.S. PATENT DOCUMENTS

| | | | |
|---|---|---|---|
| 5,891,400 A | 4/1999 | Ansari et al. | |
| 6,236,807 B1 | 5/2001 | Ruffolo et al. | |
| 6,511,531 B1* | 1/2003 | Cartellone | A61L 9/03 261/142 |
| 6,556,272 B1* | 4/2003 | Du | A61L 9/035 352/85 |
| 2002/0068010 A1* | 6/2002 | Laudamiel-Pellet | A01M 1/2033 422/5 |
| 2003/0007887 A1 | 1/2003 | Roumpos et al. | |
| 2003/0097936 A1* | 5/2003 | Maleeny | A61L 9/012 95/285 |
| 2003/0168751 A1 | 9/2003 | Bartsch et al. | |
| 2005/0074358 A1 | 4/2005 | Hart et al. | |
| 2005/0094988 A1 | 5/2005 | Yip et al. | |
| 2005/0147523 A1* | 7/2005 | Laudamiel-Pellet | A01M 1/2077 422/5 |
| 2005/0169813 A1* | 8/2005 | D'Amico | A61L 9/042 422/124 |
| 2005/0285538 A1* | 12/2005 | Jaworski | A61L 9/03 315/76 |
| 2008/0318177 A1* | 12/2008 | Requejo | A61L 9/03 431/291 |
| 2009/0004614 A1 | 1/2009 | Furner et al. | |
| 2009/0148342 A1* | 6/2009 | Bromberg | A01N 59/00 422/37 |
| 2010/0021855 A1* | 1/2010 | Requejo | A61L 9/037 431/291 |
| 2010/0059601 A1* | 3/2010 | Bankers | A01M 1/2077 239/44 |
| 2010/0178042 A1 | 7/2010 | Neumann et al. | |
| 2010/0269826 A1 | 10/2010 | Colombo et al. | |
| 2011/0049259 A1 | 3/2011 | Beland et al. | |
| 2011/0253798 A1 | 10/2011 | Tucker et al. | |

(Continued)

OTHER PUBLICATIONS

International Search Report for PCT Application No. PCT/US2014/041377 Issued Sep. 9, 2014, 4 pgs.

(Continued)

*Primary Examiner* — Thor Campbell
(74) *Attorney, Agent, or Firm* — Gardere Wynne Sewell L.L.P.

(57) ABSTRACT

Solid fragrance carriers are received in a cavity in between a replaceable shell and a permeable screen of a base that is further housing a heating element, a vertical portion of a ventilation channel and a fan. The solid fragrance carriers are evenly directly aerated by a forced air stream that is evenly heated by passing through the screen positioned around and irradiated by the central heating element. A large storage capacity of the cavity provides for long operation time between refills. Design freedom of the replaceable shell provides for associative shell shapes adaptable to varying themes, characters or consumer goods. The screen and shell may be light permeable for a decorative illumination of the solid fragrance carriers, which may be also color coded for visual scent mixture identification. Conventional liquid fragrance carriers may also be contained in a chalice at the top of the base.

15 Claims, 5 Drawing Sheets

(56) References Cited

U.S. PATENT DOCUMENTS

| | | | |
|---|---|---|---|
| 2011/0286726 A1 | 11/2011 | Baraky | |
| 2012/0024975 A1* | 2/2012 | Sharma | A01M 1/2044 239/6 |
| 2012/0199665 A1 | 8/2012 | Neumann | |
| 2014/0377130 A1* | 12/2014 | Edwards | A61L 9/02 422/5 |
| 2015/0010293 A1* | 1/2015 | Newman | A61L 9/032 392/393 |
| 2015/0017071 A1* | 1/2015 | McMinn | C11C 5/00 422/125 |

OTHER PUBLICATIONS

Written Opinion for PCT Application No. PCT/US2014/041377 Issued Sep. 9, 2014, 5 pgs.

International Search Report for Co-Pending PCT Application No. PCT/US2015/028473 mailed Jul. 22, 2015, 2 pgs.

Written Opinion for Co-Pending PCT Application No. PCT/US2015/028473 mailed Jul. 22, 2015, 6 pgs.

* cited by examiner

MODULAR MULTIFUNCTION FRAGRANCE EMITTER

FIELD OF INVENTION

The present invention relates to fragrance emitters. More particular, the present invention relates to fragrance emitters for solid fragrance carriers.

BACKGROUND OF INVENTION

Fragrance emitters are commonly configured to receive and evaporate fragrance from liquid and/or liquefiable fragrances such as water, oil or wax based fragrance solutions. A state of the art device of the present inventor for example utilizes a wig suspended from a closed fragrance container into a ventilation shaft through which ambient air is forced by a fan. Using the wig for fragrance carrier transport in conjunction with forced aeration is already a substantial improvement for controlled and interruptible scent emission compared to other devices that utilize only a chalice on top of a heating element. Nevertheless, the wig still requires some handling and occasional replacement. Also, the liquid fragrance solution requires somewhat careful handling.

Solid fragrance carriers to the contrary are much more simple to handle. Commonly available are various wooden or plastic shapes such as cubes or spheres that are saturated with a fragrance solution that gradually and continuously evaporates. Nevertheless, scent emission of such solid fragrance carriers is presently only interrupted by packing away the solid fragrance carriers. Hence, there exists a need for a fragrance emitting device that is configured for receiving solid fragrance carriers and for controlled releasing their scent. The present invention addresses this need.

Human scent recognition is far more nuanced than would be commercially viable to cover with a number of premixed scent compositions. Like in a paint shop that mixes a custom color from some few basic colors, it is desirable to have a scent delivery system for simple customizable scents. The present invention addresses also this need.

Scent recognition is highly associative. For advertising and other combined associative scent and object representation applications, it is desirable to have a system available that is easily adapted to convey various associative scent and object combinations. The present invention addresses also this need.

SUMMARY

A modular fragrance emitter has a base with a central heating element and a shell with a fragrance dispense opening. The shell rests on the base and is held in position by a permeable screen that preferably extends upward surrounding the heating element. A fragrance carrier cavity is defined between the permeable screen and the shell that is preferably filled with solid fragrance carriers of homogeneous shape, size and scent content as are well known in the art.

A ventilation channel is open to ambient air at its bottom end and terminates at a fragrance dispense opening that is preferably at the top of the shell. The permeable screen is placed at some point across the ventilation channel such that the ambient air that has entered the ventilation channel has to pass through it before the air continues through the fragrance carrier cavity.

Since the permeable screen is positioned around the heating element, it is irradiative heated by it and passes its heat on to the air. In that way a simple and save heat transfer is established that allows the heating element in the preferred configuration of a well known light bulb to remain contact free. At the same time, the large contact area of the permeable screen provides for an efficient and balanced heat transfer onto the air. This is important to facilitate balanced warming of the solid fragrance carriers and provides for a design freedom of the fragrance carrier cavity. Quantities of solid fragrance carriers that are a multiple of liquid fragrance carrier in similar sized fragrance emitters can be accommodated for that way. Consequently, fragrance emitting periods can be extended from commonly a few hours to several days and weeks. The design freedom of the fragrance carrier cavity provides also for varyingly shaped shells that may be combined with the base. Different shell shapes associable with varying themes, characters or consumer goods may thereby be employed for specific and changing occasions and applications.

The shell and permeable screen may further be light permeable. In case of the heating element being a light bulb or any other illumination means being centrally employed, the centrally emitted light may pass through the permeable screen and illuminate the solid fragrance carriers, which in turn will shine through the shell in their illuminated condition. This effect may be employed for decorative purposes and/or to visually convey the scent composition as may be color coded onto the individual solid fragrance carriers.

In a customizable scent delivery system, a number of solid fragrance carriers may be provided with basic scent configuration that may be color coded onto the solid fragrance carriers. That way custom scents may be easily composed by merely counting and combining various base scent solid fragrance carriers. There composition may be visually verified in their illuminated condition. In a combined object and related scent advertising system, the solid fragrance carriers may be of an associative fragrance designed in conjunction with an associatively shaped shell. As a theme example, the shell may resemble a Christmas tree and the solid fragrance carriers may contain fir fragrance.

DETAILED DESCRIPTION

Figure 1:
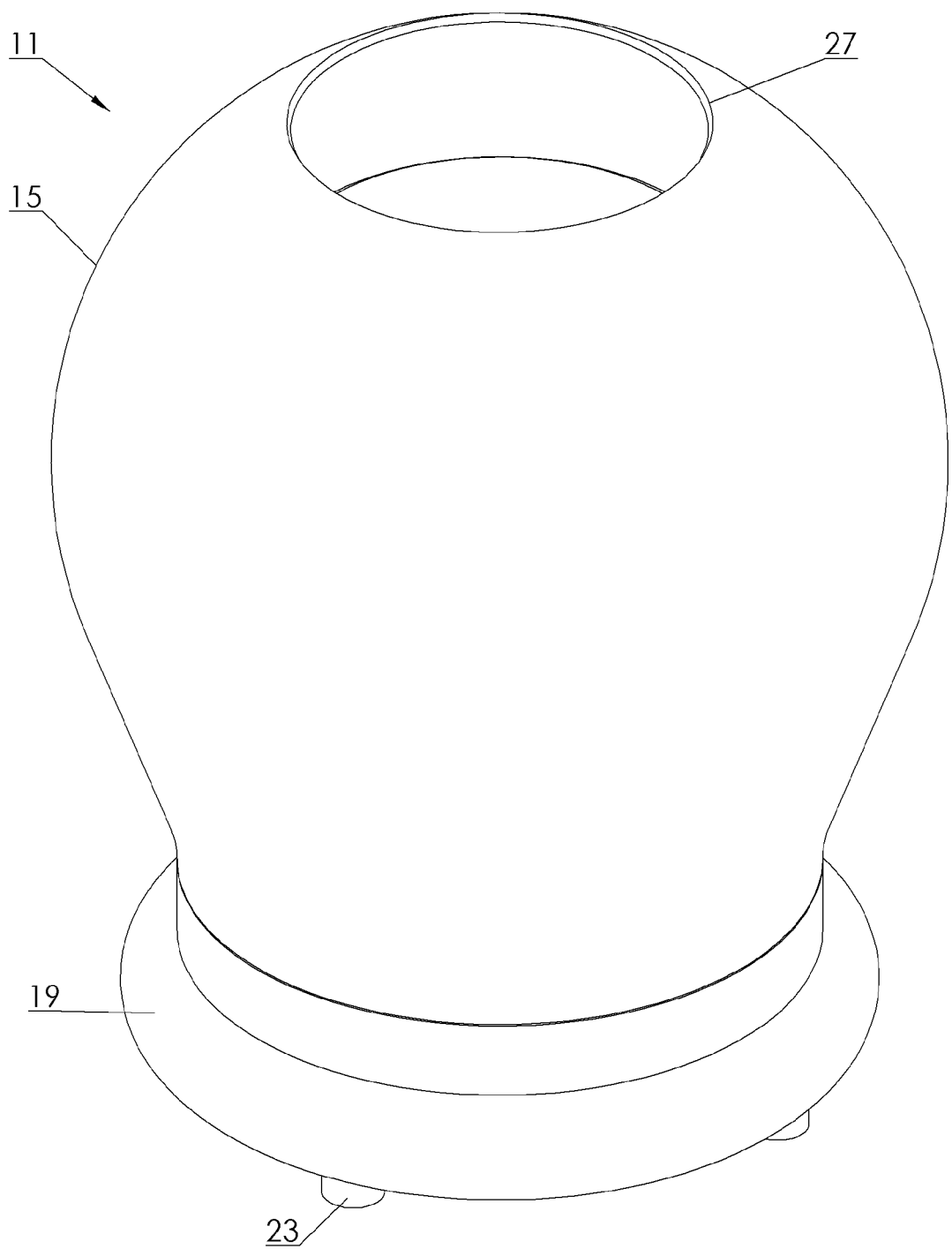
FIG. 1 is a perspective view of a preferred embodiment of the invention.
Figure 2:
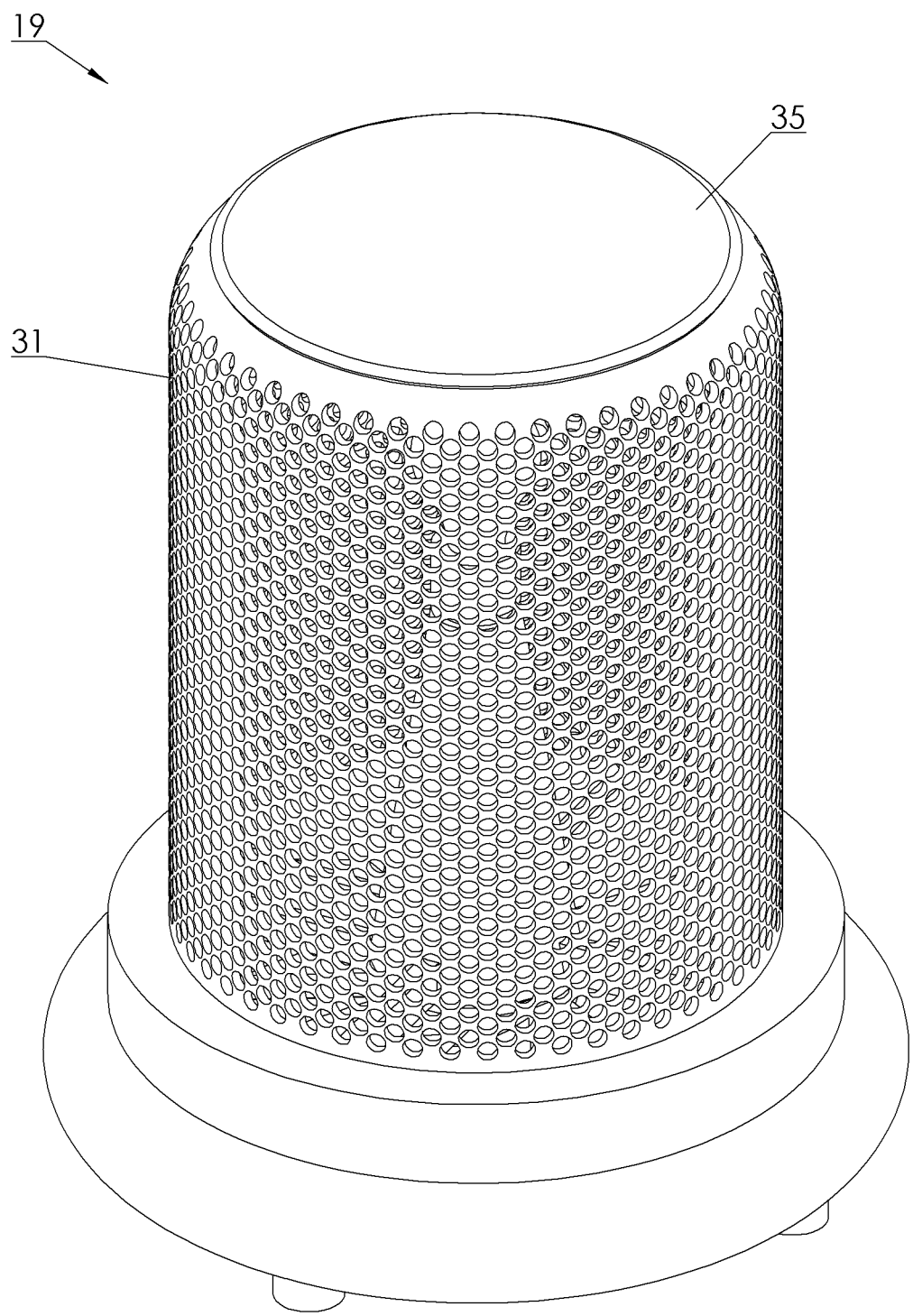
FIG. 2 is the perspective view of FIG. 1 without shell.

A modular fragrance emitter 11 features a base 19 and a shell 15 that is resting on the base 19. The shell 15 has a fragrance dispense opening 27 and preferably rests on the base 19 but may be also in any other well known way connected to it within the scope of this invention. The base 19 has a heating element 55 in the preferred configuration of a light bulb, a permeable screen 31 and a ventilation channel 47. The permeable screen 31 is at least adjacent but preferably surrounds the heating element 55 such that it is irradiative heated by the heating element 55 upon actuation by the heating element preferably by electricity as is well known in the art. The ventilation channel 47 terminates with one end at the fragrance dispense opening 27 and has an air inlet 45 on the other end. The ventilation channel 47 passes through the permeable screen 31 such that ambient air taken in at the air inlet 45 is directed towards and through the permeable screen 31. The air is thereby conductively heated by the permeable screen 31 while the heating element is actuated and irradiating the permeable screen 31. The permeable screen 31 may be of a thermally conductive material such as metal, such that irrespective eventual local irradiation peaks and induced thermal energy peaks due to closer proximity to the heating element are evenly distributed and the entire permeable screen 31 remains at substantially the same temperature. Because of that and due to a preferably homogeneous air permeability of the permeable screen 31, the ambient air passing through the permeable screen 31 is evenly heated. At the same time, the permeable screen 31 provides a large cross section area with balanced air flow restriction such that air passes through the permeable screen 31 with substantially equal speed. Equal air flow speed and air temperature are a prerequisite for an even direct aeration and heating and consequently fragrance gassing of the solid fragrance carriers 59 that are contained in a fragrance carrier cavity 17 that is preferably in between the shell 15 and the permeable screen 31 and that is preferably configured for receiving solid fragrance carriers 59 through its fragrance dispense opening 27. For the purpose of clarity in FIG. 3, only a few solid fragrance carriers 59 are depicted at the bottom of the fragrance carrier cavity 17. The permeable screen 31 is a boundary of the fragrance carrier cavity 17 such that the solid fragrance carriers 59 are at least partially contained via the permeable screen 31 and such that the ambient air is immersing the solid fragrance carriers 59 after passing through and being heated by the permeable screen 31. The fragrance emitter cavity 17 may at least partially outside contained by the shell 15.

Figure 3:
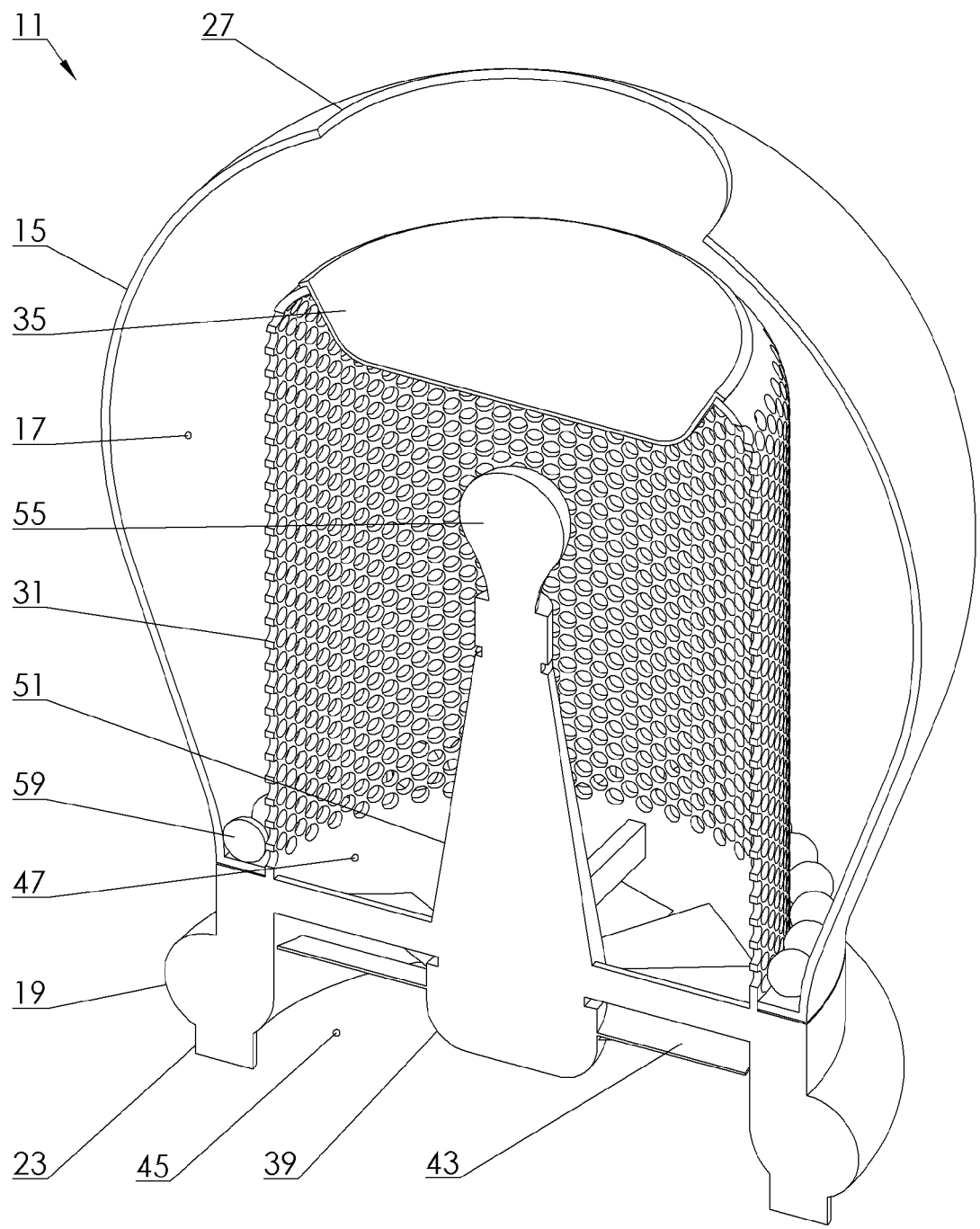
FIG. 3 is the perspective view of FIG. 1 cut along a vertical plane.

The ventilation channel 47 has preferably an overall vertical orientation such that a natural thermally induced air flow may occur while the heating element is actuated as should be clear to anyone of average skill in the art. Due to a certain air flow restriction of the permeable screen 31 and in the absence of any thermally induced buoyant air flow, the solid fragrance carriers 59 remain substantially free of aeration when the heating element 55 is not actuated. Thus, fragrance release is simply controlled by turning on and off the central heating element 55. Thermally induced air flow may be further assisted by a fan as shown in FIG. 3 with fan motor 39 and fan blades 43. The fan 39, 43 is inside the ventilation channel 47 and is part of the base 19. It is preferably mounted at the bottom of a base core 51 that holds the heating element 55 at its top. The base core 51 is held at the center of a vertical portion of the ventilation channel 47. The permeable screen 31 and the shell 15 may be at least partially light permeable such that light emitted from a light source adjacent the fragrance carrier cavity is at least partially illuminating the solid fragrance carriers 59 through the permeable screen and such that the illuminated solid fragrance carriers 59 are at least partially visible through the shell 15.

At the bottom of the base 19 may extend feet 23 that keep the base 19 in a spacing above the ground where the modular fragrance emitter 11 may be placed. Ambient air may pass through the ring shaped spacing into the air inlet 45. Having the ambient air enter preferably at the very bottom of the modular fragrance emitter 11 and exit at the very top through the fragrance dispense opening 27 provides for a maximum buoyancy effect and natural thermally induced air flow for a given height of the modular fragrance emitter 11 as should be clear to anyone skilled in the art. At the same time, the preferably overall concentric arrangement of the ventilation channel 47 and the fragrance carrier cavity 17 contributes to an overall highly balanced aeration of the solid fragrance carriers 59. This is another important aspect for a balanced fragrance depletion of the solid fragrance carriers 59.

The modular fragrance emitter 11 may further feature a fragrance carrier cavity 35 in the configuration of a chalice for containing a liquefiable fragrance carrier 71 such as well known wax cubes or other well known water or oil based fragrance solutions as are commonly employed. The chalice 35 is preferably removable positioned above the heating element 55 at the top of the base 19 with the ventilation channel 47 passing over the open chalice top and with the fragrance dispense opening 27 above the chalice 35. With such arrangement, aeration of the recessed chalice 35 is also substantially reduced without air flow through the ventilation channel 47 and fragrance release better controlled than in conventional fragrance emitters with openly held chalices as may be well appreciated by anyone skilled in the art.

The modular configuration of the fragrance emitter 11 with the base 19 in the direct balanced heating and aeration configuration as described above provides for a design freedom of the shell 19 to be shaped independently of the base 19 with a theme, character and/or consumer good associative shape as may be well understood in the art of advertising and the like.

Figure 4:
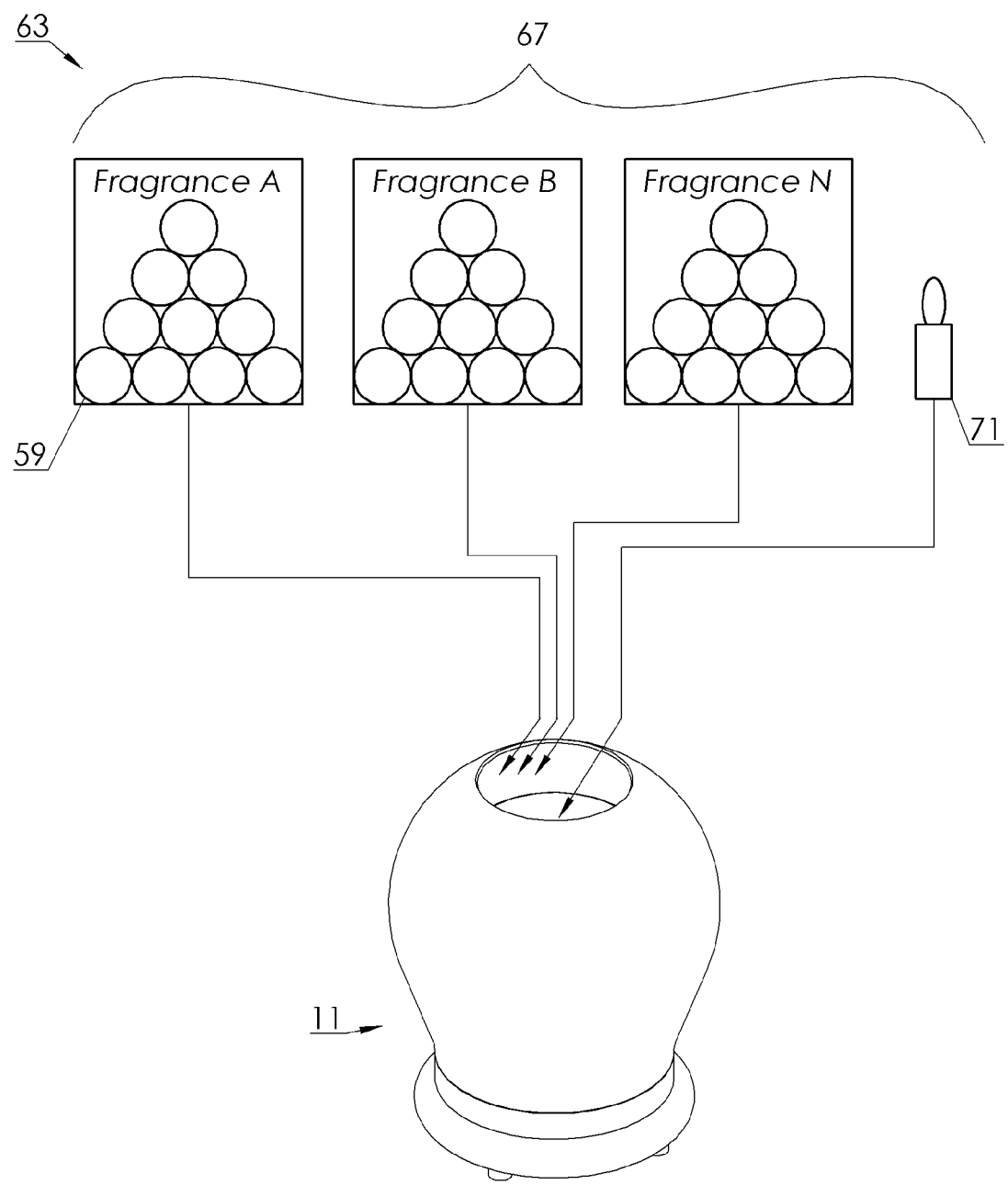
FIG. 4 is a system schematic of a second embodiment of the invention.

Referring to FIG. 4, the modular fragrance emitter 11 with its solid fragrance carrier direct heating and aeration configuration may be part of a customizable scent emitting system 63 that also includes a number of solid fragrance carriers 59 and eventually liquefiable fragrance carriers 71 configured as base fragrance carriers 67 that may be applied to the modular fragrance emitter 11 in customizable mixture compositions and their fragrances combined and controlled released as described above. The solid base fragrance carriers 59/67 may be color coded in accordance with their base fragrance such that in case of the above described fragrance carrier cavity 17 illumination the customized mixture composition is visually identifiable inside the modular fragrance emitter 11. In this system, theme, character and/or consumer good associative shells may be additionally employed.

Figure 5:
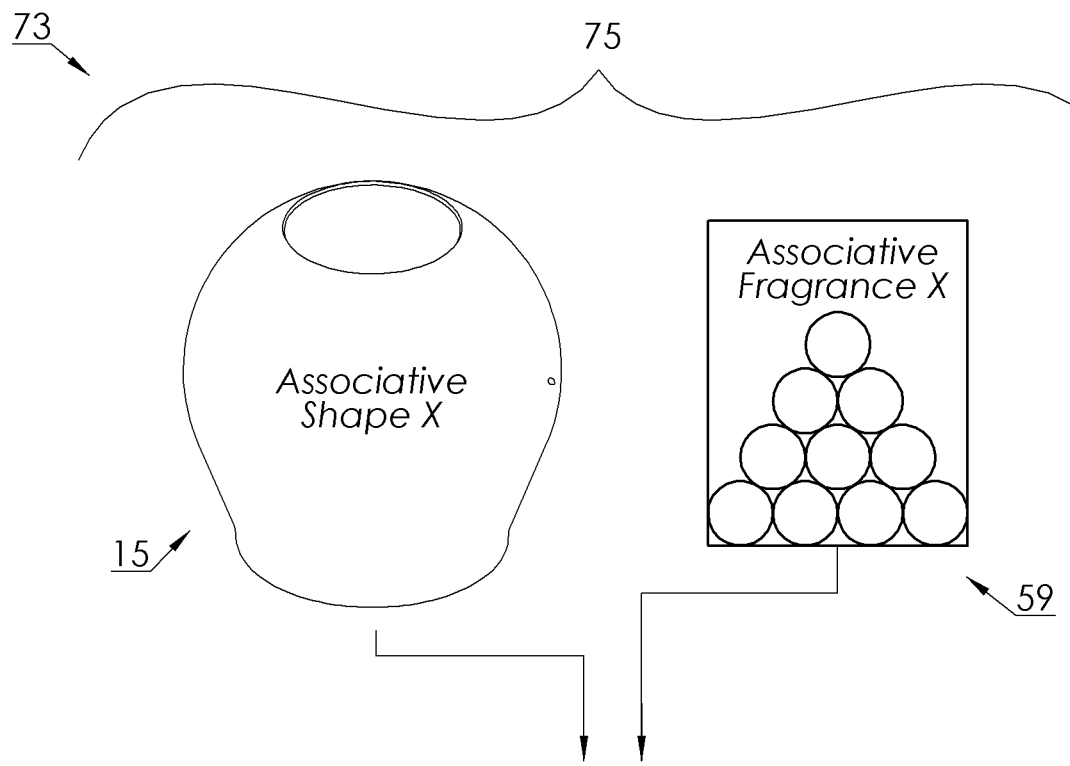
FIG. 5 is a system schematic of a third embodiment of the invention.
Figure 5:
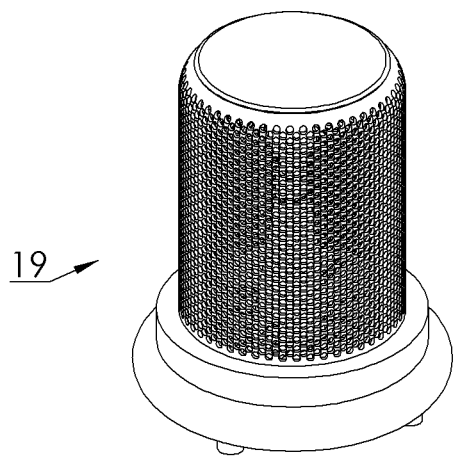

Referring to FIG. 5, a combined object and related scent advertising system 73 may feature the base 19 with its solid fragrance carrier direct heating and aeration configuration described above and an associative shape/scent set 75 including the shell 15 having an associative theme, character and/or consumer good shape and including the solid fragrance carriers 59 having a associative fragrance related to the selected associative shell 15 shape. For example of a character associative shape/scent set, the shell 15 may be shaped like a head of a well known comic book superhero and the associative fragrance may be selected to be associated with the effect of his particular superpower. For example of a consumer good associative shape/scent set, the shell 15 may be shaped like a well known chocolate product and the associative fragrance may be selected to be associative with that chocolate product.

To operate the modular fragrance emitter 11 and/or the systems 63, 73, a selected shell 15 may be placed on the base 19 thereby establishing the fragrance carrier cavity 17 for solid fragrance carriers 59 and establishing the complete ventilation channel 47. This may be done at factory site and/or at end user site. A selected solid fragrance carrier 59 group or mixture composition may then be filled preferably through the fragrance dispense opening into the fragrance carrier cavity 17. Optionally and in addition or alternatively, a conventional liquefiable fragrance carrier 71 may be placed in the eventual chalice 35. The heating element 55 may be actuated by preferably connecting it to an electricity source, which will start aeration and heating of the fragrance carriers 59, 71. Optionally, the fan 39, 43 may also be actuated together with the heating element 55 by also connecting it to an electricity source. Fragrance evaporates then and is emitted through the fragrance dispense opening until the heating element 55 and eventually the fan 39, 43 are turned off again. Then heating and aeration is stopped and substantially no fragrance emitted.

What is claimed is:

1. A modular fragrance emitter comprising:
   a base including a heating element;
   a permeable screen coupled to the base and positioned around the heating element;
   a shell coupled to the base and having a fragrance dispense opening; and
   a fragrance carrier cavity formed between the permeable screen and the shell to contain a plurality of solid fragrance carriers positioned within at least a portion of the fragrance carrier cavity,
   wherein the permeable screen is configured to be selectively irradiative heated by activating the heating element, and
   wherein the heating element is configured to generate a thermally induced airflow through the plurality of solid fragrance carriers to emit the fragrance.

2. The modular fragrance emitter of claim 1, wherein the base further comprises:
   a ventilation channel extending from a first end at the fragrance dispense opening to a second end at an air inlet on the base, wherein the ventilation channel passes through the permeable screen such that ambient air taken in at the air inlet is directed towards and through the permeable screen, and is thereby conductively heated by the permeable screen while the heating element is activated to generate the thermally induced airflow.

3. The modular fragrance emitter of claim 2, wherein the base further comprises a fan connected to the ventilation channel, wherein the fan is configured to blow the ambient air through the permeable screen.

4. The modular fragrance emitter of claim 2, wherein the permeable screen includes a chalice positioned above the heating element and configured to contain a liquefiable fragrance carrier, and wherein an open top of the chalice is adjacent the ventilation channel such that the ambient air passes over the open top.

5. The modular fragrance emitter of claim 1, wherein the permeable screen and the shell are at least partially light permeable such that light emitted from a light source adjacent the fragrance carrier cavity is at least partially illuminating at least a portion of the solid fragrance carriers through the permeable screen and such that the illuminated solid fragrance carriers are at least partially visible through the shell.

6. The modular fragrance emitter of claim 1, wherein the shell comprises a theme shape.

7. The modular fragrance emitter of claim 1, wherein the shell comprises a character shape.

8. The modular fragrance emitter of claim 1, wherein the shell comprises a consumer good shape.

9. A customizable scent emitting system comprising:
   a modular fragrance emitter, the modular fragrance emitter including:
      a base having a heating element,
      a permeable screen coupled to the base and positioned around the heating element,
      a shell coupled to the base and having a fragrance dispense opening, and
      a fragrance carrier cavity formed between the permeable screen and the shell; and
   a plurality of solid fragrance carriers comprising a base fragrance and configured for being contained, heated, and aerated within the modular fragrance emitter in customizable mixture compositions.

10. The customizable scent delivery system of claim 9, wherein the solid fragrance carriers having the base fragrance are color coded in accordance with their base fragrance.

11. The customizable scent delivery system of claim 9, wherein the shell comprises a theme.

12. The customizable scent delivery system of claim 9, wherein the shell resembles a character.

13. The customizable scent delivery system of claim 9, wherein the shell resembles a consumer good.

14. The customizable scent delivery system of 9, wherein the permeable screen is configured to be selectively irradiative heated by activating the heating element.

15. The customizable scent delivery system of claim 9, wherein the heating element is configured to generate a thermally induced airflow through the plurality of solid fragrance carriers to emit the base fragrance.

* * * * *